(12) United States Patent
Liu et al.

(10) Patent No.: US 11,473,115 B2
(45) Date of Patent: Oct. 18, 2022

(54) **EXOPOLYSACCHARIDE FROM *RHODOPSEUDOMONAS PALUSTRIS* AND METHOD FOR PREPARING AND USE THEREOF**

(71) Applicants: Hunan Plant Protection Institute, Hunan (CN); Changsha Agreen Bio-Tech Ltd., Co., Hunan (CN); Suzhou Ace Chemical Technology Co., Ltd., Jiangsu (CN)

(72) Inventors: Yong Liu, Hunan (CN); Pin Su, Hunan (CN); Zhongying Zhai, Hunan (CN); Zhuo Zhang, Hunan (CN); Haixing Yang, Jiangsu (CN); Jianping Dai, Hunan (CN); Bo Zhou, Hunan (CN); Deyong Zhang, Hunan (CN); Ju'e Cheng, Hunan (CN)

(73) Assignees: Hunan Plant Protection Institute, Hunan (CN); Changsha Agreen Bio-Tech Ltd., Co., Hunan (CN); Suzhou Ace Chemical Technology Co., Ltd., Jiangsu (CN)

(*) Notice: Subject to any disclaimer, the term of this patent is extended or adjusted under 35 U.S.C. 154(b) by 0 days.

(21) Appl. No.: 17/265,097

(22) PCT Filed: Nov. 11, 2020

(86) PCT No.: PCT/CN2020/128092
§ 371 (c)(1),
(2) Date: Feb. 1, 2021

(87) PCT Pub. No.: WO2021/184780
PCT Pub. Date: Sep. 23, 2021

(65) Prior Publication Data
US 2022/0042058 A1 Feb. 10, 2022

(30) Foreign Application Priority Data

Mar. 17, 2020 (CN) .......................... 202010187236.6

(51) Int. Cl.
| | | |
|---|---|---|
| C12P 19/04 | (2006.01) |
| A01N 63/20 | (2020.01) |
| A01N 31/06 | (2006.01) |
| C12R 1/01 | (2006.01) |
| A01P 17/00 | (2006.01) |

(52) U.S. Cl.
CPC .............. *C12P 19/04* (2013.01); *A01N 31/06* (2013.01); *A01N 63/20* (2020.01); *A01P 17/00* (2021.08); *C12R 2001/01* (2021.05)

(58) Field of Classification Search
None
See application file for complete search history.

(56) References Cited

U.S. PATENT DOCUMENTS

2019/0032035 A1  1/2019  Bujnicki et al.
2019/0307818 A1  10/2019  Bassler et al.

FOREIGN PATENT DOCUMENTS

| CN | 1631372 A | 6/2005 |
|---|---|---|
| CN | 104403978 A | 3/2015 |
| CN | 104498399 A | 4/2015 |
| CN | 105794853 A | 7/2016 |
| CN | 106135285 A | 11/2016 |
| CN | 108409877 A | 8/2018 |
| CN | 110294794 A | 10/2019 |
| EP | 2171047 A1 | 4/2010 |
| WO | 2018090288 A1 | 5/2018 |
| WO | 2019083316 A2 | 5/2019 |
| WO | 2019179110 A1 | 9/2019 |

OTHER PUBLICATIONS

Yin et al. "Biodegradation of Cypermethrin by Rhodopseudomonas Palustris GJ-22 Isolated From Activated Sludge" Fresenius Environmental Bulletin, vol. 21, no1 21, 2012 (Year: 2012).*
NCBI "Symbol Nomenclature for Glycans (SNFG)" https://www.ncbi.nlm.nih.gov/glycans/snfg.html, 10 pags, Aug. 31, 2016 (Year: 2016).*
Machine English Translation of Zang, Peng, "Preparation, Structure Characterization and Biological Activities of an Extracellular Polysaccharide from Rhodopseudomonas Palustris," Northwest A&F University, China, 2019. 62 pages, IDS Jul. 8, 2021 NPL#2. (Year: 2019).*
Zhang, Peng, "Preparation, Structure Characterization and Biological Activities of an Extracellular Polysaccharide from Rhodopseudomonas Palustris," Northwest A&F University, China, 2019.
Zhai, Zhongying, et al. "A genetic tool for production of GFP-expressing *Rhodopseudomonas palustris* for visualization of bacterial colonization," AMB Expr 9, 141,2019.

* cited by examiner

*Primary Examiner* — Thane Underdahl
(74) *Attorney, Agent, or Firm* — Calfee Halter & Griswold LLP

(57) ABSTRACT

The invention discloses an exopolysaccharide from *Rhodopseudomonas palustris* and a method for preparing and use thereof, and the method for preparing comprises the steps of: 1) keeping a seed solution from *Rhodopseudomonas palustris* GJ-22 in a fermentation medium for fermentation culture to obtain a fermentation broth; 2) centrifuging the fermentation broth to take the supernatant, which is treated by alcohol precipitation after filtration, and then collecting the pellet from alcohol precipitation by centrifugation to obtain crude polysaccharide; 3) removing proteins from the rude polysaccharide using protease enzymolysis method and Sevag method, followed by dialysis treatment with distilled water to remove small molecules and organic solvent to obtain a polysaccharide sample; 4) purifying the polysaccharide sample through an anion exchange column and a molecular exclusion chromatography column obtain the exopolysaccharide from *Rhodopseudomonas palustris*.

8 Claims, 9 Drawing Sheets

EXOPOLYSACCHARIDE FROM *RHODOPSEUDOMONAS PALUSTRIS* AND METHOD FOR PREPARING AND USE THEREOF

CROSS-REFERENCE TO RELATED APPLICATIONS

This application is a 371 of PCT Application No. PCT/CN2020/128092 filed on Nov. 20, 2020, which claims priority to Chinese Application No. 2020101872366 filed on Mar. 17, 2020, the contents of which are hereby incorporated by reference as if recited in their entirety.

TECHNICAL FIELD

The invention relates to the technical field of biological pesticide, in particular to an exopolysaccharide from *Rhodopseudomonas palustris*. Furthermore, the present invention also relates to a method for preparing above exopolysaccharide from *Rhodopseudomonas palustris* and its use in promoting the growth of plant as well as preventing and controlling diseases and the like.

BACKGROUND ART

For the prevention and control of plant diseases, chemical prevention and control are currently the main focus, which causes major problems such as environmental pollution and agricultural product quality and safety and the like due to increased resistance and untimely discovery, unscientific pesticide application, the dosage and frequency of pesticide application exceeding the standard etc. In recent years, biological prevention and control has attracted more and more attention in the prevention and control of plant diseases and pests due to its advantages of non-toxic, harmless, non-polluting, difficult to produce resistance and high efficiency. Microbial-derived biopesticides have developed rapidly, but few studies have been conducted on which part of the microorganisms are effective in promoting the growth of plant and inhibiting plant diseases and pests, which is very disadvantageous for the development of targeted and efficient biopesticides.

Exopolysaccharides from microorganisms are water-soluble or water-insoluble polysaccharides that are synthesized by some bacteria and fungi during their growth on various carbon sources and secreted outside the cells. Compared with polysaccharides from plant and marine algae, exopolysaccharides from microorganisms have the advantages of short growth cycle, unaffected by climate, simple production process, low cost, convenient mass preparation and the like. Exopolysaccharides from microorganisms are widely used in medicine, chemical industry, petroleum exploration, environmental protection and the like due to their general characteristics of non-toxic, unique structure, stable physical and chemical properties etc., and some of them having activities in antioxidant, immune suppression, immune promotion, anti-tumor and so on. Therefore, it will be beneficial to develop an exopolysaccharides from microorganisms that can be used for promoting the growth of plant and biological prevention and control to replace abused chemical pesticides.

SUMMARY OF THE INVENTION

The present invention provides an exopolysaccharide from *Rhodopseudomonas palustris* and a method for preparing and use thereof, in order to solve the technical problem that the effect of biological prevention and control is not good enough due to the unclear specific active component in the existing biological prevention and control.

According to one aspect of the present invention, provided is an exopolysaccharide from *Rhodopseudomonas palustris* having the structural formula of:

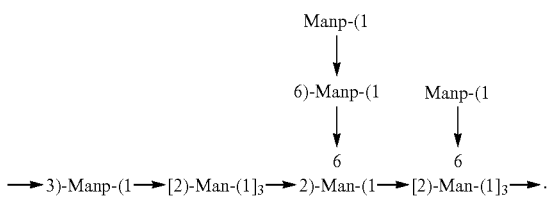

Further, the exopolysaccharide is extracted by alcohol precipitation from *Rhodopseudomonas palustris* GJ-22 fermentation broth.

According to another aspect of the present invention, provided is a method for preparing the above exopolysaccharide from *Rhodopseudomonas palustris*, comprising the steps of:

1) keeping a seed solution from *Rhodopseudomonas palustris* GJ-22 in a fermentation medium for fermentation culture to obtain a fermentation broth;

2) centrifuging the fermentation broth to take the supernatant, which is treated by alcohol precipitation after removal of suspended matters by membrane filtration, and then collecting the pellet from alcohol precipitation by centrifugation to obtain crude polysaccharide using lyophilization;

3) removing proteins from the rude polysaccharide using protease enzymolysis method and Sevag method, followed by dialysis treatment with distilled water to remove small molecules and organic solvent to obtain a polysaccharide sample;

4) purifying the polysaccharide sample through an anion exchange column and a molecular exclusion chromatography column in sequence to obtain the exopolysaccharide from *Rhodopseudomonas palustris*.

Further, in step 1), the components of the fermentation medium comprise: $(NH_4)_2SO_4$ 0.1 g, $MgSO_4$ 0.02 g, $Na_2CO_3$ 0.5 g, $K_2HPO_4$ 0.05 g, NaCl 0.02 g, casein amino acid 0.2 g, agar 1.5 g, at pH of 7.0-7.5, the fermentation culture is carried out with a light intensity of 7000 lx-8000 lx at the temperature of 30° C. for 10 days.

Further, in step 2), the alcohol precipitation comprises the steps of adding anhydrous ethanol at a volume of twice that of the filtered supernatant with a placement at 4° C. for 24 h following stirring well, collecting by centrifugation with a centrifugal force of 10000-13000 g, preferably 10000 g at 4° C. for 20 min.

Further, in step 3), the protease enzymolysis method comprises the steps of: dissolving the crude polysaccharide obtained in step (2) in deionized water with addition of papain to obtain a sample, which is adjusted to pH 6.0-6.2 and treated in a water bath at 60° C. for 6 h, during which the obtained sample is shaken once every 1 hour for mixing well, with addition of anhydrous ethanol at a volume of twice that of the obtained sample after cooling, and then collecting the pellet by centrifugation after placement.

Further, the dialysis treatment uses a dialysis bag with a molecular weight cut-off of 8000 D-14000 D.

Further, in step 4), Hi Trap Q Sepharose High Performance is used as the anion exchange column, Seharose CL-6B chromatography column is used as the molecular exclusion chromatography column.

According to another aspect of the present invention, further provided is use of above exopolysaccharide from *Rhodopseudomonas palustris* in promoting the growth of tobacco or rice.

According to yet another aspect of the present invention, further provided is use of above exopolysaccharide from *Rhodopseudomonas palustris* in preventing and controlling tobacco mosaic virus or rice blast.

The present invention has the following beneficial effects:

The method for preparing the exopolysaccharide from *Rhodopseudomonas palustris* GJ-22 provided by the present invention obtains the exopolysaccharide from *Rhodopseudomonas palustris* GJ-22 with simple production process, stable expression and easy to obtain by fermentation culture, alcohol precipitation, separation and purification. The present invention is the first to study the foliar exopolysaccharide from bacteria for prevention and control. The study finds that the purified exopolysaccharide from *Rhodopseudomonas palustris* GJ-22 can significantly promote the growth of plant and enhance the disease resistance of plant superior to the *Rhodopseudomonas palustris* GJ-22 itself, therefore, this provides a possibility for the development of a biocontrol agent, which will provide an important use value in the agricultural field.

In addition to the objectives, features, and advantages described above, the present invention has other objectives, features, and advantages. The present invention will be described in further detail with reference to the drawings.

BRIEF DESCRIPTION OF THE DRAWINGS

The drawings constituting a part of the present application are used to provide a further understanding of the present invention, and the exemplary embodiments and descriptions of the present invention are used to explain the present invention, and do not limit inappropriately the present invention. In the drawings.

DETAILED DESCRIPTION OF EMBODIMENTS

Figure 1:
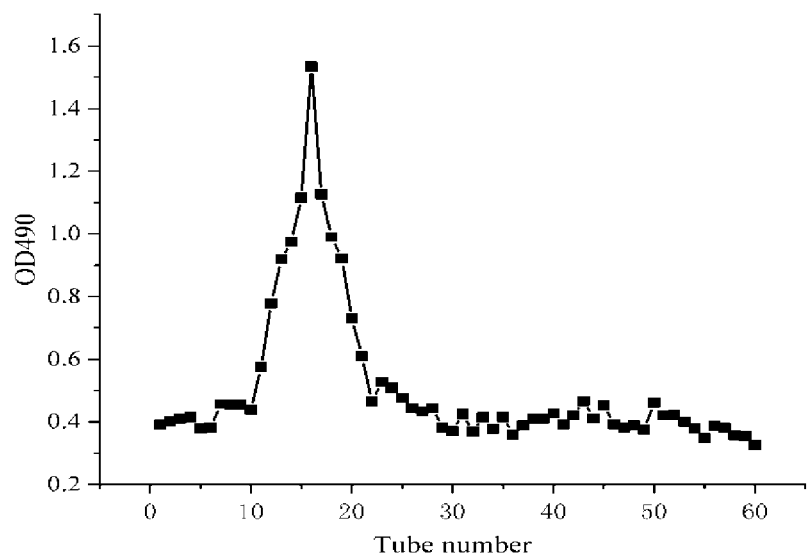
FIG. 1 is a schematic diagram of the elution curve of a polysaccharide anion exchange column in a preferred embodiment of the present invention.

The embodiments of the present invention will be described in detail below with reference to the accompanying drawings, but the present invention may be implemented in a variety of different ways defined and covered below.

The materials and instruments used in the following examples are all commercially available.

Example 1

Preparation and purification of the exopolysaccharide from *Rhodopseudomonas palustris*

The microorganism of the present invention was *Rhodopseudomonas palustris* GJ-22, a foliar biocontrol bacteria, which was obtained by separation and purification from water, and deposited in the China General Microbiological Culture Collection Center located at Institute of Microbiology Chinese Academy of Sciences, Building No. 3, 1 Beichen West Road, Chaoyang District, Beijing 100101 on Mar. 19, 2019 with CGMCC Deposit No: 17356.

In this embodiment, the method for preparing the exopolysaccharide from *Rhodopseudomonas palustris* GJ-22 comprised the following steps:

1). a seed solution from *Rhodopseudomonas palustris* GJ-22 was kept in a fermentation medium for fermentation culture to obtain a fermentation broth; the method for obtaining the seed solution was as follows: *Rhodopseudomonas palustris* GJ-22 was activated in a plate, followed by picking a single colony for seed culture for 4 days to obtain the seed solution. The seed solution was inoculated into the fermentation medium with 10% inoculum for fermentation culture with a light intensity of 7000 lx-8000 lx at the temperature of 30° C. for 10 days;

2). the fermentation broth was centrifuged with a centrifugal force of 15000 g at 4° C. for 50 min to take the supernatant, the purpose of which was to separate the remaining bacteria and insoluble impurities; the supernatant was treated by alcohol precipitation after removal of suspended matters by membrane filtration, and then the pellet from alcohol precipitation was collected by centrifugation to obtain crude polysaccharide using lyophilization; a 0.45 μm membrane was preferred, which was used to filter out very small suspended particles in the supernatant after centrifugation;

3). proteins were removed from the rude polysaccharide using protease enzymolysis method and Sevag method, followed by dialysis treatment with distilled water to remove small molecules and organic solvent to obtain a polysaccharide sample;

4). the polysaccharide sample was purified through an anion exchange column and a molecular exclusion chromatography column in sequence to obtain the exopolysaccharide from Rhodopseudomonas palustris.

The method for preparing the exopolysaccharide from Rhodopseudomonas palustris GJ-22 provided by the present invention obtained the exopolysaccharide from Rhodopseudomonas palustris GJ-22 with simple production process, stable expression and easy to obtain by fermentation culture, alcohol precipitation, separation and purification. The present invention was the first to study the foliar exopolysaccharide from bacteria for prevention and control. The study found that the purified exopolysaccharide from Rhodopseudomonas palustris GJ-22 could significantly promote the growth of plant and enhance the disease resistance of plant superior to the Rhodopseudomonas palustris GJ-22 itself, therefore, this provided a possibility for the development of a biocontrol agent, which would provide an important use value in the agricultural field.

In this example, in step 1), the components of the fermentation medium comprised: $(NH_4)_2SO_4$ 0.1 g, $MgSO_4$ 0.02 g, $Na_2CO_3$ 0.5 g, $K_2HPO_4$ 0.05 g, NaCl 0.02 g, casein amino acid 0.2 g, agar 1.5 g, at pH of 7.0-7.5. The fermentation medium of this example was added with the casein amino acid to increase the production of extracellular polysaccharides.

In this example, in step 2), the alcohol precipitation comprises the specific steps of adding anhydrous ethanol at a volume of twice that of the filtered supernatant with a placement at 4° C. for 24 h following stirring well, and collecting the pellet from alcohol precipitation by centrifugation with a centrifugal force of 10000-13000 g, preferably 10000 g at 4° C. for 20 min. The pellet was preferably washed three times with anhydrous ethanol to remove impurities, followed by lyophilization to obtain crude polysaccharide. The crude polysaccharide was collected by alcohol precipitation to obtain the extracted polysaccharides with higher purity, more complete and stable structure.

In this example, in step 3), the protease enzymolysis method for removal of proteins comprised the steps of: dissolving the crude polysaccharide obtained in step (2) in an appropriate amount of deionized water (the amount of deionized water based on the total dissolution of the crude polysaccharide) with addition of papain to obtain a sample, which was adjusted to pH 6.0-6.2 and treated in a water bath at 60° C. for 6 h, during which the obtained sample was shaken once every 1 hour for mixing well, with addition of anhydrous ethanol at a volume of twice that of the obtained sample after cooling, and then collecting the pellet by centrifugation after placement. Papain could decompose proteins under acidic, neutral and alkaline conditions, with activities of protease and esterase and strong hydrolysis ability on the exopolysaccharide from bacteria, and would not damage the structure of the exopolysaccharide, so that the extracted exopolysaccharide had a higher content.

The Sevag method for removal of proteins comprised the steps of: dissolving the polysaccharide treated with protease in an appropriate amount of deionized water (the amount of deionized water based on the total dissolution of the polysaccharide) with addition of ¼ (v/v) sevag reagent (chloroform: n-butanol=5:1), followed by shaking vigorously for 2 h and centrifuging at 10000 g for 10 min to remove denatured proteins at the junction of the water phase and the organic phase.

In this example, in step 3), the dialysis treatment used a dialysis bag with a molecular weight cut-off of 8000 D-14000 D. Specifically, the protein-removed polysaccharide was packed into a dialysis bag with a molecular weight cut-off of 8000-14000 D, dialyzed with distilled water for 2 days with changing the water every 4 h to remove small molecular compounds and organic solvent. After the dialysis, the sample was concentrated under reduced pressure and treated by lyophilization to obtain a polysaccharide sample.

In this example, in step 4), Hi Trap Q Sepharose High Performance was used as the anion exchange column, Seharose CL-6B chromatography column was used as the molecular exclusion chromatography column.

The specific operation of anion exchange column purification was as follows: the protein-removed polysaccharide sample was purified through an anion exchange column after being dissolving in an appropriate amount of distilled water. The anion exchange column was Hi Trap Q Sepharose High Performance (1.6×2.5 cm, GE Healthcare), with a loading volume of 5 mL, a loading concentration of 20 mg/mL, a flow rate of 5 mL/min, and a 2 mL centrifuge tube for collection. Firstly, the column was washed with Tris-HCl (20 Mm, pH 7.60) for two column volumes, followed by eluting with a gradient of 0.5 M Tris-HCl and 0.5 M NaCl. The polysaccharide content was detected by the phenol-sulfuric acid method tube by tube, with the number of tubes collected as the abscissa, and the absorbance of each tube at 490 nm as the ordinate to depict an elution curve, as shown in FIG. 1. The tubes with the same sugar content were pooled, and dialyzed with distilled water for 2 days to remove small molecules, followed by concentrating the dialysate under reduced pressure and treating by lyophilization to obtain purified components. The specific operation of Seharose CL-6B column chromatography purification was as follows: the components purified by the anion exchange column were dissolved in a balance solution, which was an elution buffer (20 mM PBS) prepared as 20 mg/mL polysaccharide solution with removal of insoluble parts by centrifugation. The supernatant was injected into the injection inlet with a syringe with a loading volume of 2 mL after being filtered through a 0.22 μm membrane, followed by eluting for 2 volumes using the elution buffer and collecting the sample automatically. The sample was dialyzed in distilled water for 2 days and treated by lyophilization to obtain purified exopolysaccharide from Rhodopseudomonas palustris GJ-22.

Figure 2:
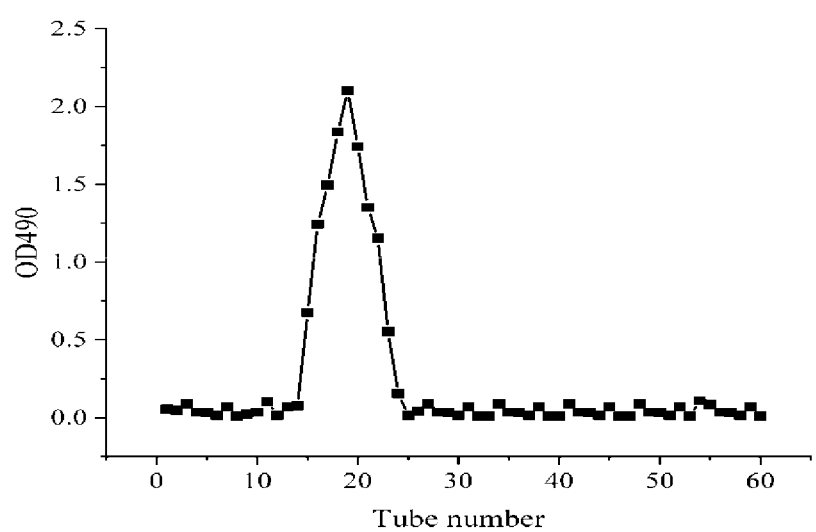
FIG. 2 is a schematic diagram of the elution curve of a Seharose CL-6B column in a preferred embodiment of the present invention.

As shown in FIG. 1, the elution peak was a single peak when eluted through the anion exchange column. As shown in FIG. 2, the elution peak was also a single peak when eluted through the Seharose CL-6B column. It could be concluded that the obtained exopolysaccharide from Rhodopseudomonas palustris GJ-22 had relatively higher purity.

Example 2

Structural identification of the exopolysaccharide from Rhodopseudomonas palustris GJ-22

The molecular weight identification of the exopolysaccharide from Rhodopseudomonas palustris GJ-22 prepared in Example 1 includes the following steps:

(1) Preparation of molecular weight standard curve of stands: different relative molecular masses of dextran (Mw1152, 11600, 23800, 48600, 80900, 148000, 273000, 409800) were used as standards (Sigma-Aldrich), using high performance liquid chromatography (Shimadzu LC-10A), with differential refractive detector for detection, and BRT105-104-102 tandem gel column 8×300 mm (Borui Saccharide, Biotech. Co. Ltd.) was used as the chromatographic column; the standard curve of the monosaccharide standards was depicted with retention time as the abscissa and relative molecular mass as the ordinate.

(2) Determination of the molecular weight of the sample: the exopolysaccharide from *Rhodopseudomonas palustris* GJ-22 (referred to as sample) was precisely weighed. The sample was prepared into a 5 mg/mL solution, centrifuged at 12000 rpm for 10 min, the supernatant from which was filtered with a 0.22 μm filter membrane, and the sample was transferred to a 1.8 mL injection vial with an injection volume of 20 μl, using a high performance liquid chromatograph (Shimadzu LC-10A), with differential refractive detector for determination the molecular weight and purity of the polysaccharide, and BRT105-104-102 series gel column 8×300 mm (Borui Saccharide, Biotech. Co. Ltd.) was used as the chromatographic column.

According to the molecular weight of a series of dextran standards, the peak time of the sample was regressed with the log MW of the standard dextran molecular weight to obtain a dextran standard curve, and then the molecular weight of the sample was calculated according to the retention time of the sample.

Figure 3:
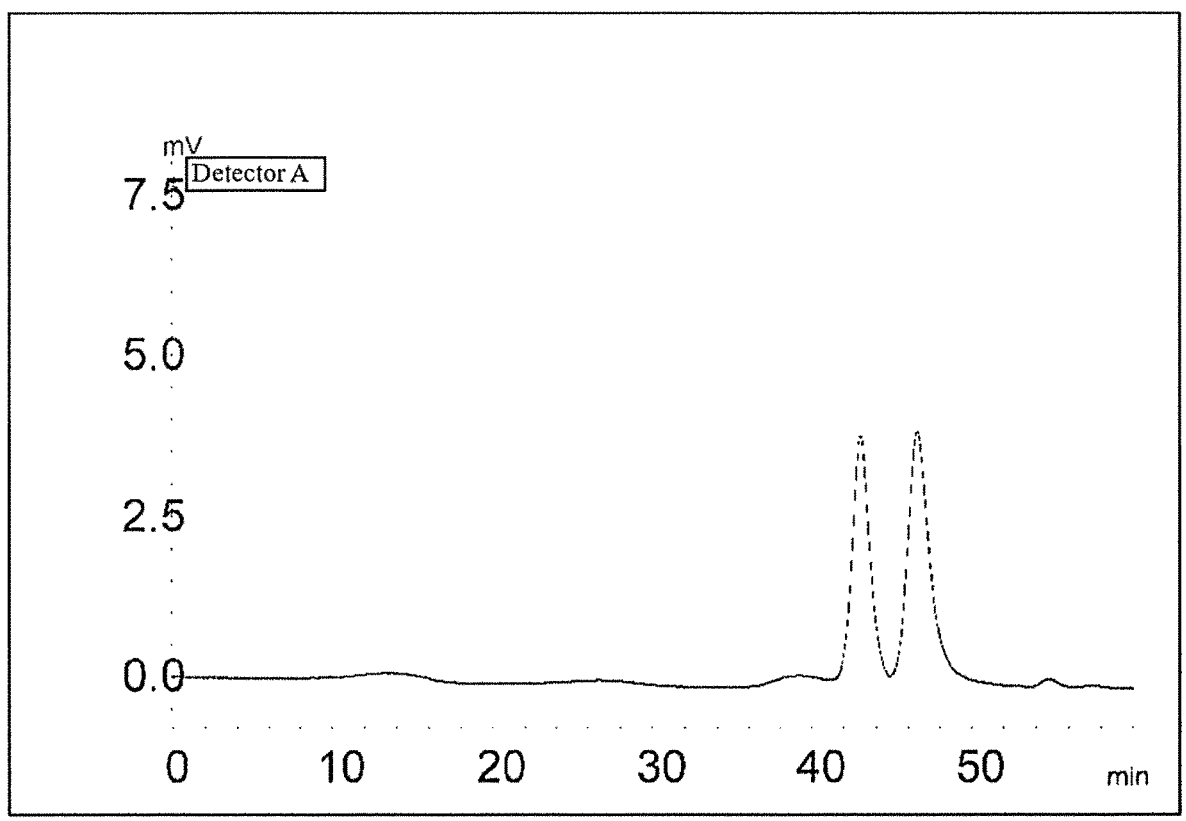
FIG. 3 is a schematic diagram of molecular weight spectrogram of the exopolysaccharide from *Rhodopseudomonas palustris* GJ-22 in a preferred embodiment of the present invention.

FIG. 3 was the measured molecular weight spectrogram of the exopolysaccharide from *Rhodopseudomonas palustris* GJ-22. The measured retention time of the sample was introduced into the standard curve of the monosaccharide standard, and the relative molecular weight of the sample was calculated to be 10026 D.

The monosaccharide component analysis of the exopolysaccharide from *Rhodopseudomonas palustris* GJ-22 prepared in Example 1 included the following steps:

(1) Complete hydrolysis of the polysaccharide: 50 mg of the exopolysaccharide from *Rhodopseudomonas palustris* GJ-22 were accurately weighed, which were dissolved in 3 mL of 2 M trifluoroacetic acid with reaction at 110° C. for 6 h under the protection of nitrogen, and then a few methanol was added and evaporated to dryness under reduced pressure after the hydrolysate being rotary evaporation, which was repeated for 5 times to remove the remaining TFA, followed by addition of a few distilled water to dissolve and treatment by lyophilization to obtain a completely hydrolyzed monosaccharide sample;

(2) Acetylation of the polysaccharide: the hydrolyzed monosaccharide sample obtained in step (1) was added to 2 mL of double-distilled water, reduced with 100 mg of sodium borohydride and neutralized by adding glacial acetic acid, followed by rotary evaporation and dryness in oven at 110° C. Then 1 mL of acetic anhydride was added for acetylation with reaction at 100° C. for 1 h, and 3 mL of toluene were added after cooling, followed by concentration under reduced pressure and evaporation to dryness, which was repeated 4 times to remove excess acetic anhydride. The acetylated product was transferred to a separatory funnel after being dissolved in 3 mL of chloroform, with addition of a few distilled water to remove the upper aqueous solution, which was repeated 5 times, and the chloroform layer was dried with an appropriate amount of anhydrous sodium sulfate to a constant volume of 10 mL.

Figure 4:
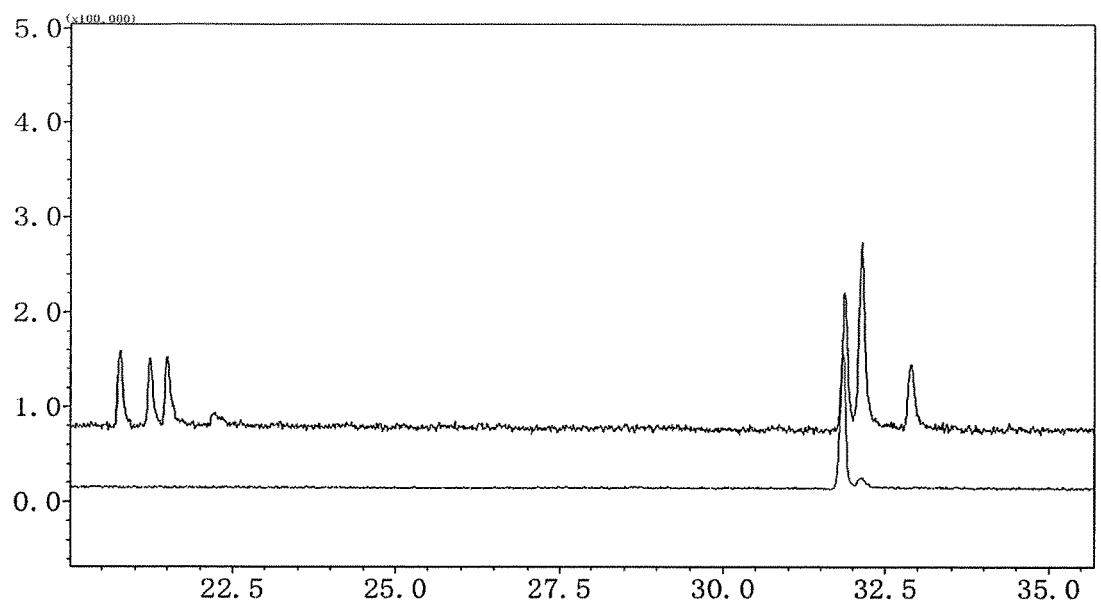
FIG. 4 is a schematic diagram of the monosaccharide composition of the exopolysaccharide from *Rhodopseudomonas palustris* GJ-22 in a preferred embodiment of the present invention.

(3) Analysis method of polysaccharide components: the product obtained in step (2) was analyzed by Shimadzu GCMS-QP 2010 gas chromatography-mass spectrometer, with GC-MS conditions as follows: RXI-5 SIL MS column 30*0.25*0.25 mm; the conditions of heating program as follows: at initial temperature of 120° C., the temperature was rose to 250° C./min at 3° C./min and maintained for 5 min, with the inlet temperature of 250° C., the detector temperature of 250° C./min, helium as the carrier gas, at a flow rate of 1 mL/min. The monosaccharide composition diagram of the obtained exopolysaccharide was shown in FIG. 4, which showed that *Rhodopseudomonas palustris* GJ-22 was composed of two monosaccharides, mannose and glucose.

Figure 5:
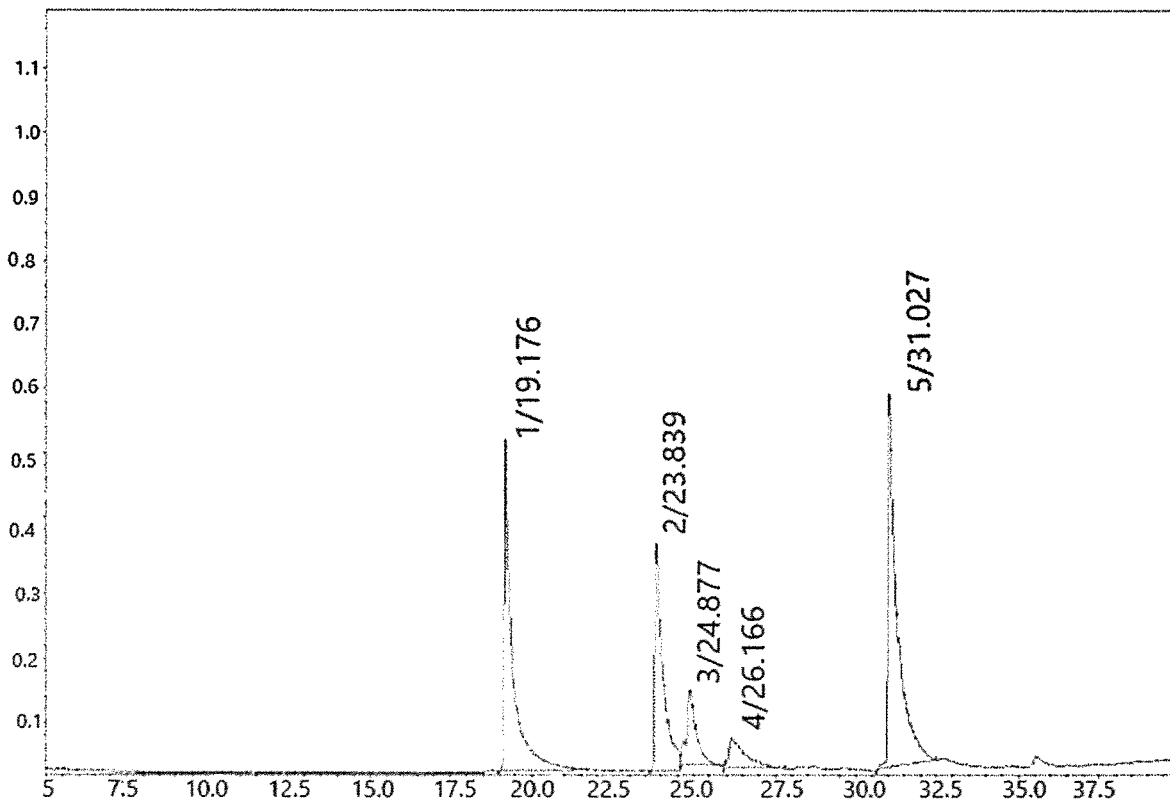
FIG. 5 is a schematic diagram of GC-MS of the exopolysaccharide from *Rhodopseudomonas palustris* GJ-22 in a preferred embodiment of the present invention.

The the exopolysaccharide from *Rhodopseudomonas palustris* GJ-22 prepared in Example 1 was subjected to methylation analysis, and the specific method included the following steps:

(1) Methylation reaction: 10 mg of the exopolysaccharide from *Rhodopseudomonas palustris* GJ-22 were added to 2 mL of anhydrous dimethyl sulfoxide to fully dissolve. The reaction flask was filled with nitrogen with placement at room temperature for 30 min, and then 10 mg of NaOH were added and filled with nitrogen again with reaction for 1 h at room temperature under magnetic stirring, followed by addition of 0.5 mL of methyl iodide, filled with nitrogen, and continued the reaction for 1 h at room temperature. After the reaction, 0.5 mL of distilled water was added to the reaction tube to terminate the reaction. The sample was dialyzed with distilled water for 24 h and treated by lyophilization, followed by continuing to be methylated until reaction complete, with addition of 3 mL of distilled water to terminate the reaction. The obtained sample was extracted three times with chloroform, 2 mL each time, then the extracts were pooled, washed twice with distilled water, with rotary evaporation to dryness, followed by addition of a few distilled water and treatment by lyophilization, which was repeated twice (2) Methyl acetate of sugar alcohol: 5 mg of the completely methylated sample obtained in step (1) were dissolved in 2 mL of 2 M TFA, with reaction for 6 h at 100° C. under nitrogen protection, followed by evaporating to dryness under reduced pressure, with addition of 3 mL of methanol with rotary evaporation to dryness, which was repeated three times. The sample was dried by a nitrogen blowing device, with addition of 0.5 mL of pyridine and reaction at 90° C. for 0.5 h, and then 0.5 mL of acetic anhydride was added with reaction at 90° C. for 4 h. After the reaction, the sample was blown dry with nitrogen to obtain fully acid hydrolyzed sugar alcohol methyl acetate. The sample was dissolved in dichloromethane and analyzed by GC-MS at conditions as follows: Shimadzu GCMS-QP 2010 gas chromatography-mass spectrometer was used to determine acetylated product samples; the GC-MS spectrogram of the exopolysaccharide from GJ-22 was shown in FIG. 5.

(3) GC-MS conditions: RXI-5 SIL MS column 30*0.25*0.25 mm; the conditions of heating program as follows: at initial temperature of 120° C., the temperature was rose to 250° C./min at 3° C./min and maintained for 5 min, with the inlet temperature of 250° C., the detector temperature of 250° C./min, helium as the carrier gas, at a flow rate of 1 mL/min.

Figure 6:
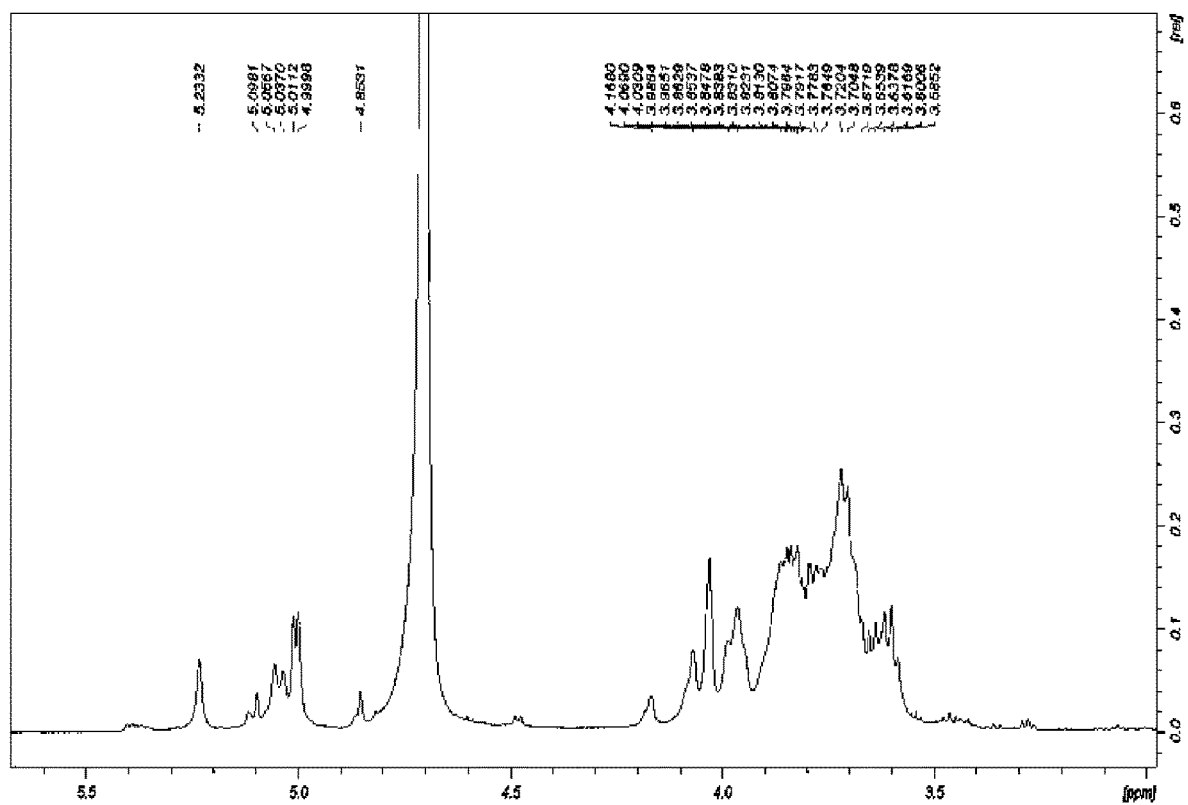
FIG. 6 is a hydrogen spectrogram of the exopolysaccharide from *Rhodopseudomonas palustris* GJ-22 in a preferred embodiment of the present invention.
Figure 7:
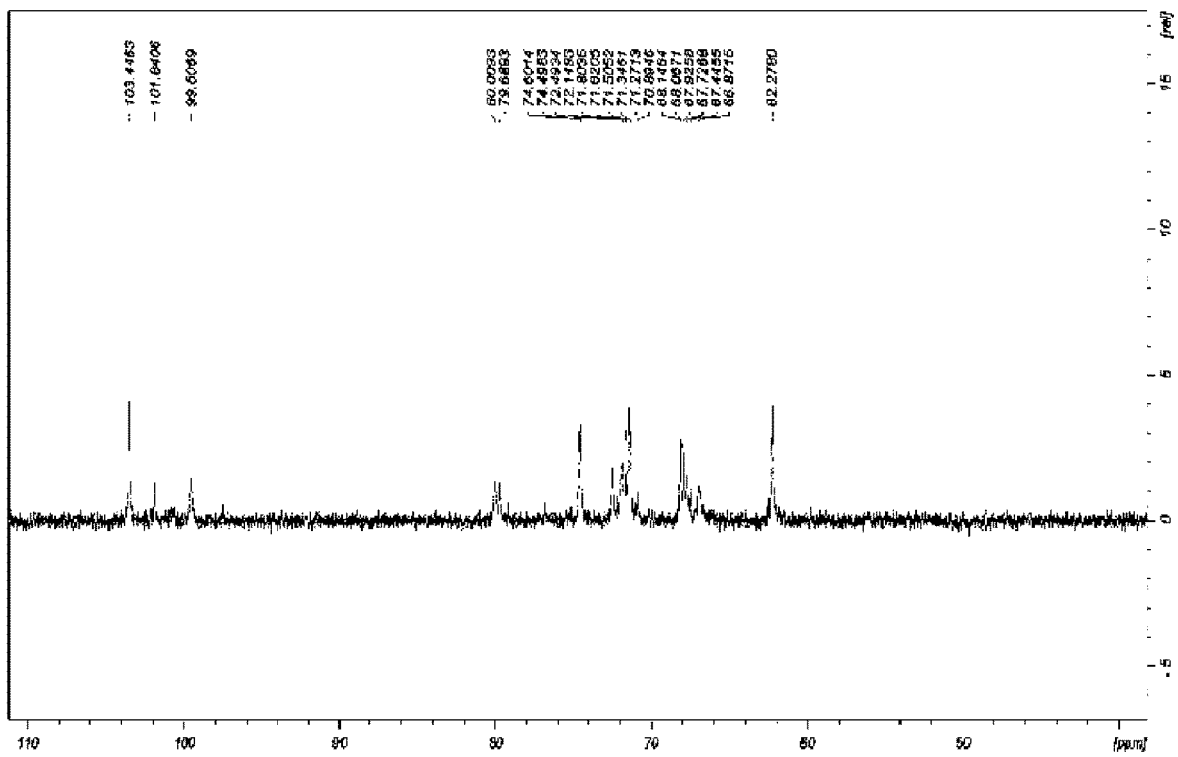
FIG. 7 is a carbon spectrogram of the exopolysaccharide from *Rhodopseudomonas palustris* GJ-22 in a preferred embodiment of the present invention.
Figure 8:
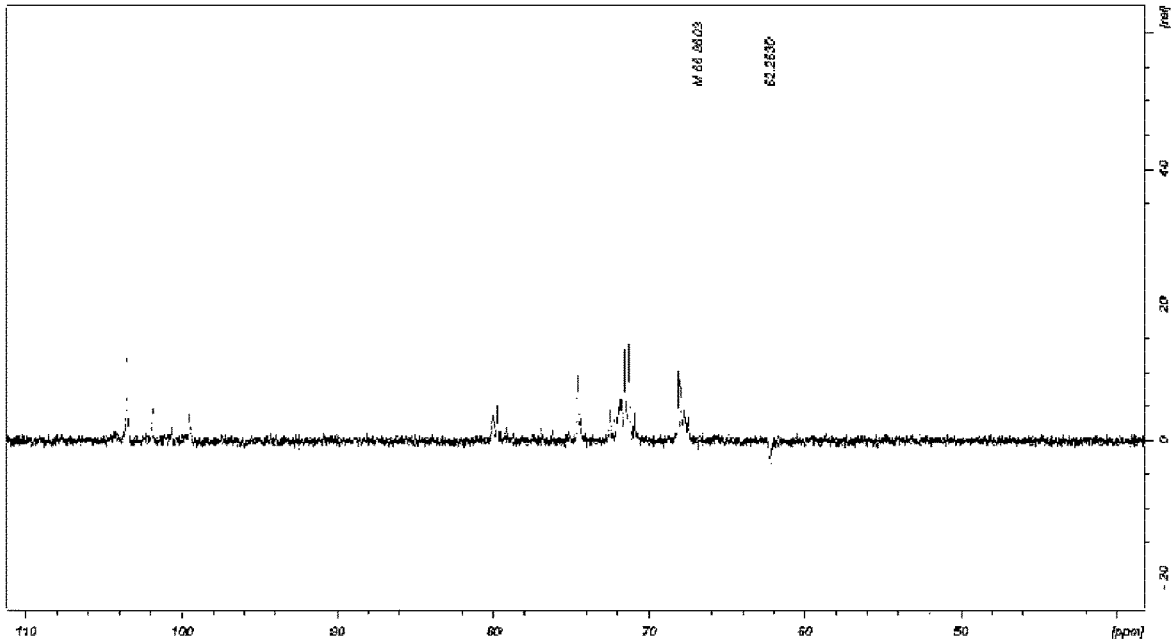
FIG. 8 is a DEPT$^{135}$ nuclear magnetic resonance spectrogram of the exopolysaccharide from *Rhodopseudomonas palustris* GJ-22 in a preferred embodiment of the present invention.
Figure 9:
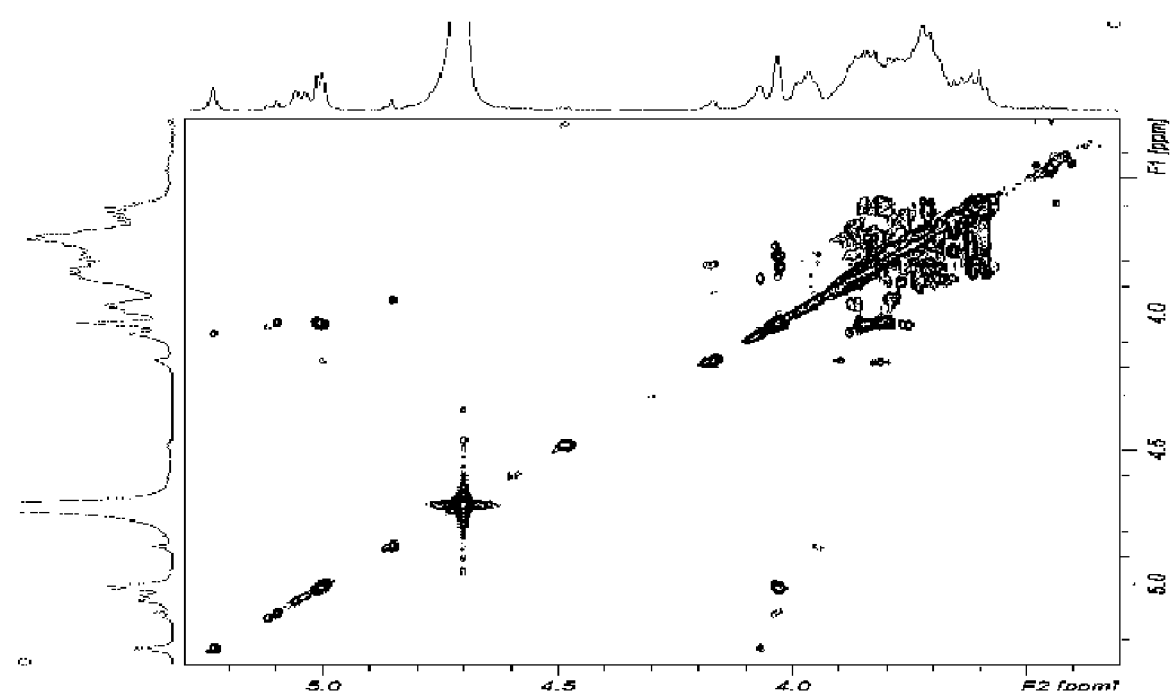
FIG. 9 is a HH-COSY spectrogram of the exopolysaccharide from *Rhodopseudomonas palustris* GJ-22 in a preferred embodiment of the present invention.
Figure 10:
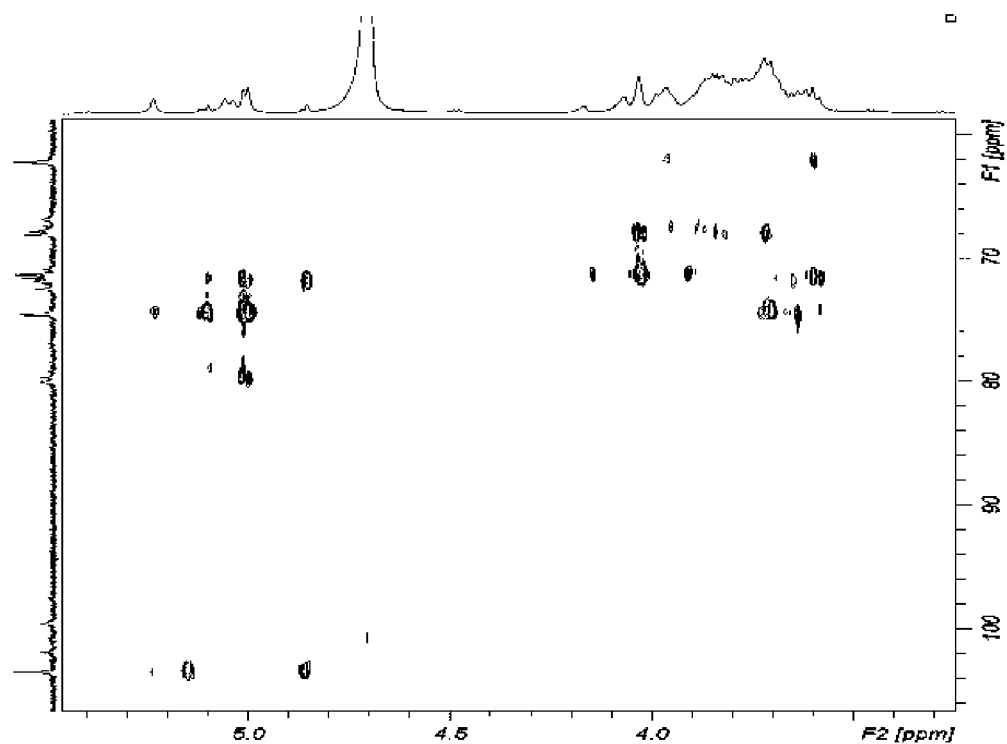
FIG. 10 is a HMBC spectrogram of the exopolysaccharide from *Rhodopseudomonas palustris* GJ-22 in a preferred embodiment of the present invention.
Figure 11:
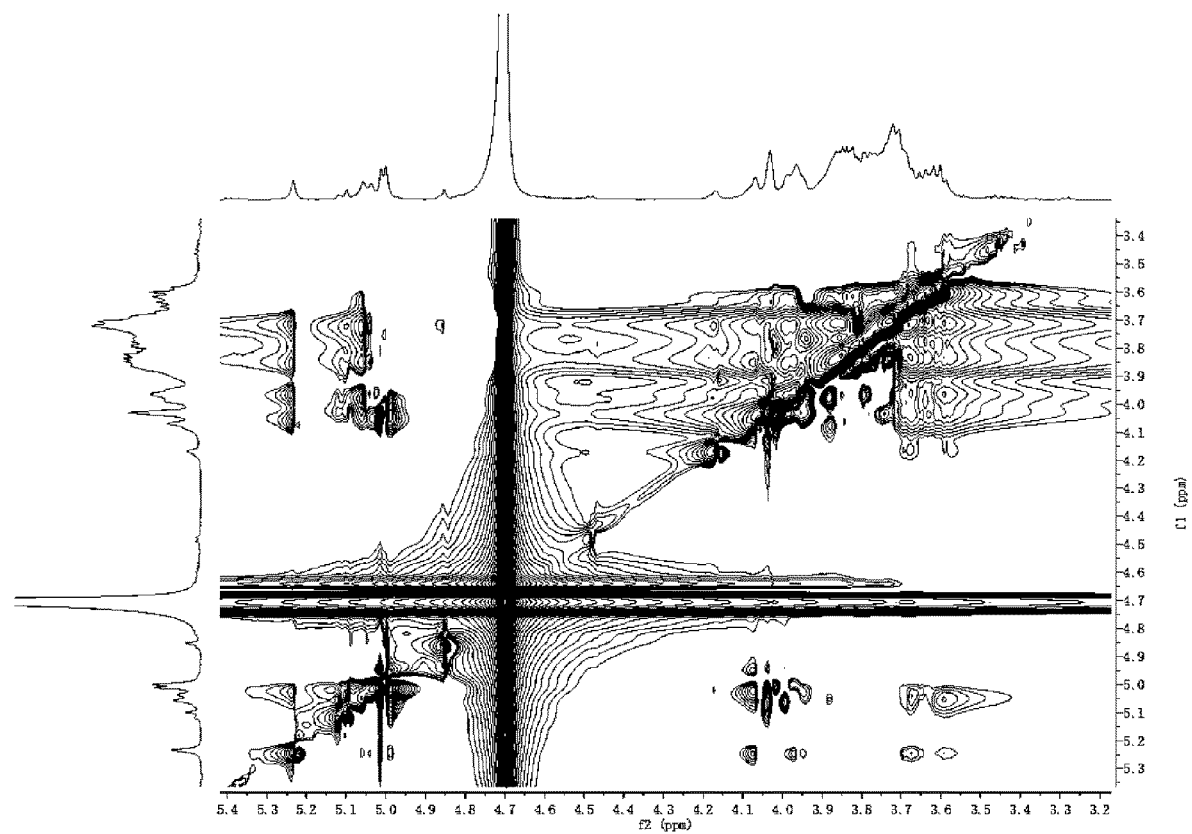
FIG. 11 is a NOESY spectrogram of the exopolysaccharide from *Rhodopseudomonas palustris* GJ-22 in a preferred embodiment of the present invention.

The exopolysaccharide from *Rhodopseudomonas palustris* GJ-22 prepared in Example 1 was subjected to NMR analysis, which specifically included the following:

NMR analysis: 100 mg of the exopolysaccharide from *Rhodopseudomonas palustris* GJ-22 were dissolved in 1 mL of D2O, and analyzed by a 600 MHz nuclear magnetic resonance instrument. The hydrogen spectrogram of the exopolysaccharide from *Rhodopseudomonas palustris* GJ-22 was shown in FIG. 6, the carbon spectrogram was shown in FIG. 7, the DEPT[135] nuclear magnetic resonance spectrogram was shown in FIG. 8, the HH-COSY spectrogram was shown in FIG. 9, the HMBC spectrogram was shown in FIG. 10, and the NOESY spectrogram was shown in FIG. 11.

According to FIGS. 6, 7, 8, 9, 10 and 11, the results of NMR analysis were as follows:

(1) $^1$H NMR: from the analysis of the hydrogen spectrogram of the sample, it could be seen that the hydrogen spectrum signal was mainly concentrated between 3.0 ppm and 5.5 ppm, δ3.2 ppm-4.0 ppm was the sugar ring proton signal, and the signal peaks of the main terminal proton peaks of δ5.23, 5.10, 5.06, 5.04, 5.01 and 4.85 were concentrated in the region of 4.3 ppm-5.5 ppm;

(2) $^{13}$C NMR: from the analysis of the carbon spectrogram of the sample, it could be seen that the carbon spectrum signal was mainly concentrated between 60 ppm and 120 ppm. By observing the carbon spectrum, the main anomeric carbon signal peaks 103.45, 101.84, 99.51 could be seen, and the anomeric carbon region was mainly in 93 ppm-105 ppm;

(3) 2D NMR: DEPT[135]: from the analysis of the DEPT[135] spectrogram of the sample, it could be seen that the peaks at 66.86 ppm and 62.26 ppm were inverted peaks, indicating the chemical shift of C6, and the peak at 66.86 ppm migrated to the low field, indicating the existence of substitution;

(4) HH-COSY: from HH-COSY, the signal of H1-2 was 5.23/4.06; the signal of H2-3 was 4.06/3.86; the signal of H3-4 was 3.86/3.79; the signal of H4-5 was 3.79/3.65; the signal of H5-6a was 3.65/3.71, inferring that H1, H2, H3, H4, H5, H6a were 5.23, 4.06, 3.86, 3.79, 3.65, 3.71, respectively, and H6b was 3.82, and the corresponding carbon spectrum was 6101.89, 79.67, 71.62, 67.74, 74.63, 62.16;

(5) HMBC: the anomeric hydrogen of →3-Man-1→ had a correlation peak with the C2 of →2-Man-1→, indicating that the presence of →3-Man-1→2-Man-1→ in the polysaccharide;

the anomeric hydrogen of →2-Man-1→ had a correlation peak with the C2 of →2,6-Man-1→, indicating the presence of →2-Man-1→2,6-Man-1→ in the polysaccharide;

the anomeric hydrogen of →2,6-Man-1→ had a correlation peak with its own C2, indicating that the presence of →2,6-Man-1→2,6-Man-1→ in the polysaccharide;

thus we could speculate the sugar link mode of: →3-Man-1→2-Man-1→2,6-Man-1→2,6-Man-1→;

(6) NOESY: the anomeric hydrogen of Man-1→ had a correlation peak with H6b of →6-Man-1→, indicating the presence of Man-1→6-Man-1→;

the anomeric hydrogen of →6-Man-1→ had a correlation peak with H6b of →2,6-Man-1→, indicating the presence of →6-Man-1→2,6-Man-1→;

Combining methylation analysis and NMR analysis, it was concluded that the structural formula of the exopolysaccharide from *Rhodopseudomonas palustris* GJ-22 prepared in Example 1 was:

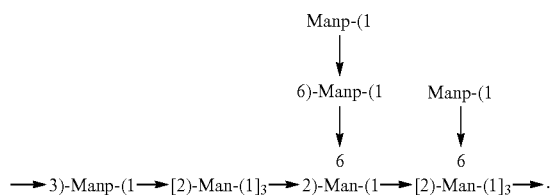

The present invention identified and obtained the structure of the exopolysaccharide from *Rhodopseudomonas palustris* GJ-22, so that the prevention and control active components of biological control more clear. Through a comprehensive and systematic study of the exopolysaccharide from *Rhodopseudomonas palustris* GJ-22, it provided a basic theory for the structure-activity relationship between the function and structure of *Rhodopseudomonas palustris* GJ-22. In addition, the exopolysaccharide from *Rhodopseudomonas palustris* GJ-22 had advantages of convenient production, stable effect and suitable for large-scale production and preparation.

Biocontrol activity and use of the exopolysaccharide from *Rhodopseudomonas palustris*

Example 3

The exopolysaccharide from *Rhodopseudomonas palustris* GJ-22 prepared in Example 1 was formulated into a 1 g/L solution, which was sprayed evenly on the tobacco leaves after transplanting for 7 days, with spraying once a day in the morning and evening to keep moist. The fresh weight of the plants was measured after 7 days, and the supernatant of the fermentation broth, fermentation medium and water of *Rhodopseudomonas palustris* GJ-22 were used for blank testing.

Example 4

The exopolysaccharide from *Rhodopseudomonas palustris* GJ-22 prepared in Example was formulated into a 1 g/L solution, which was sprayed evenly on the rice leaves after transplanting for 7 days, with spraying once a day in the morning and evening to keep moist. The fresh weight of the plants was measured after 7 days, and the supernatant of the fermentation broth, fermentation medium and water of *Rhodopseudomonas palustris* GJ-22 were used for blank testing.

Figure 12:
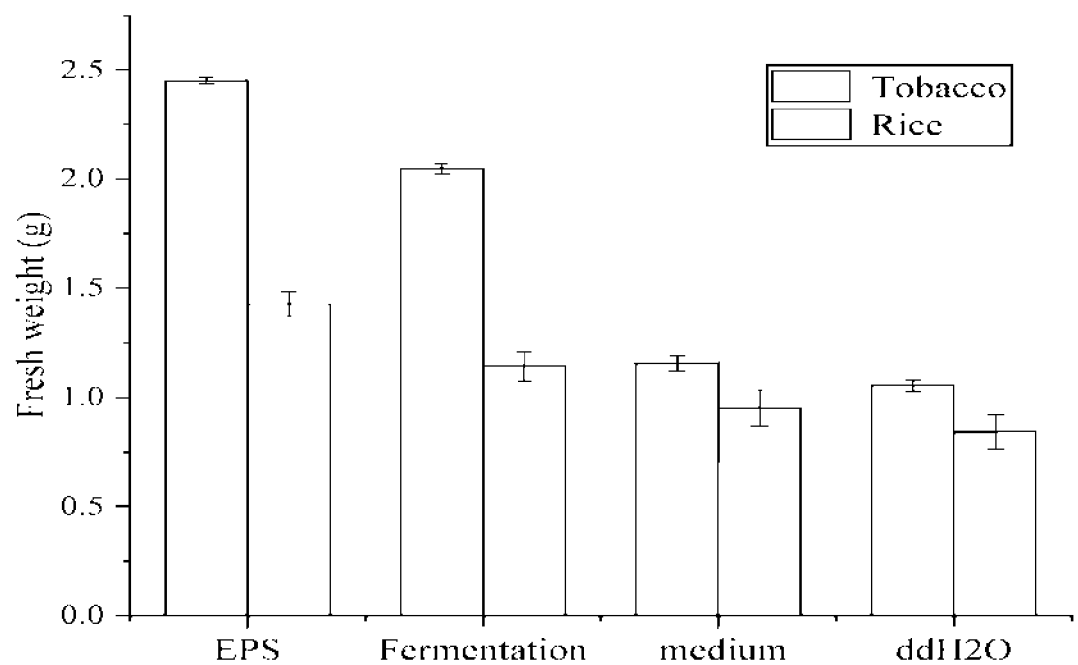
FIG. 12 is a diagram showing the fresh weight of plants treated with the exopolysaccharide from *Rhodopseudomonas palustris* GJ-22 in a preferred embodiment of the present invention.

FIG. 12 was a diagram showing the fresh weight of tobacco and rice treated with the exopolysaccharide from *Rhodopseudomonas palustris* GJ-22 in Example 3 and Example 4. *Rhodopseudomonas palustris* GJ-22 was represented by EPS, the supernatant of the fermentation broth of *Rhodopseudomonas palustris* was represented by Fermentation, the fermentation medium was represented by medium, the water was represented by ddH2O, the tobacco was represented by Tobacco, and the rice was represented by Rice. It could be seen from FIG. 12 that the exopolysaccharide from *Rhodopseudomonas palustris* GJ-22 could significantly promote the growth of tobacco and rice, and its growth promotion effect was superior to that of the fermentation broth supernatant and fermentation medium of *Rhodopseudomonas palustris*.

Example 5

Figure 13:
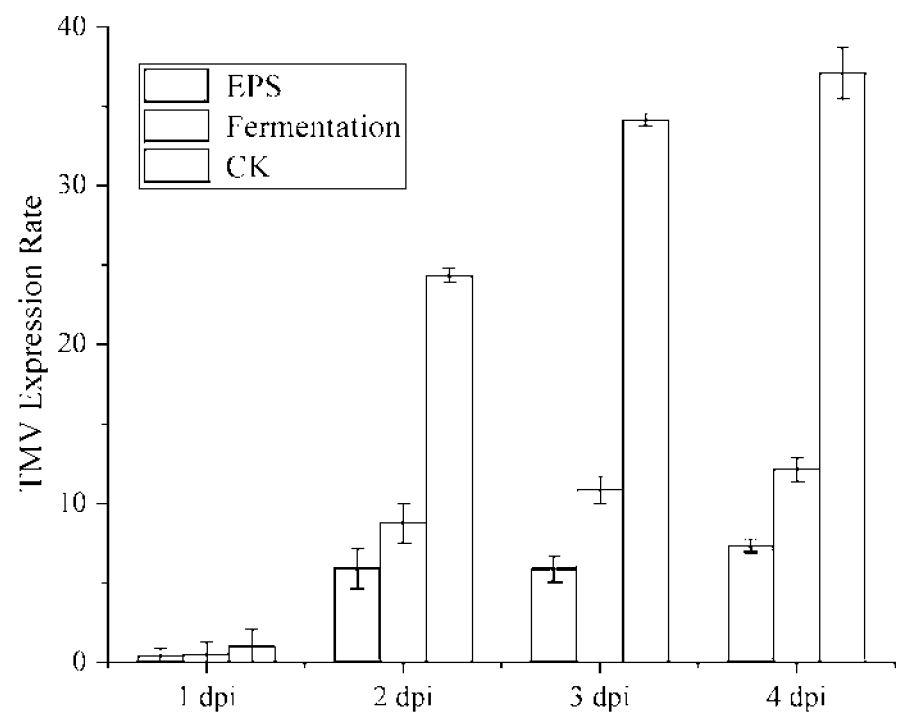
FIG. 13 is a detection diagram of inducing tobacco resistance to TMV virus particles by the exopolysaccharide from *Rhodopseudomonas palustris* GJ-22 in a preferred embodiment of the present invention.

The exopolysaccharide from *Rhodopseudomonas palustris* GJ-22 prepared in Example 1 was formulated into a 1 g/L solution and sprayed on the surface of healthy tobacco leaves with six leaves. The TMV virus particles were rubbed and inoculated on the second day. The plant RNA was extracted and the number of TMV virus particles in the plant was determined at days 1, 2, 3 and 4 after inoculation. As shown in FIG. 13, the supernatant of the fermentation broth of *Rhodopseudomonas palustris* and the water were used for blank testing.

FIG. 13 showed that the exopolysaccharide from *Rhodopseudomonas palustris* GJ-22 could significantly enhance the resistance of tobacco to the virus TMV.

Example 6

Figure 14:
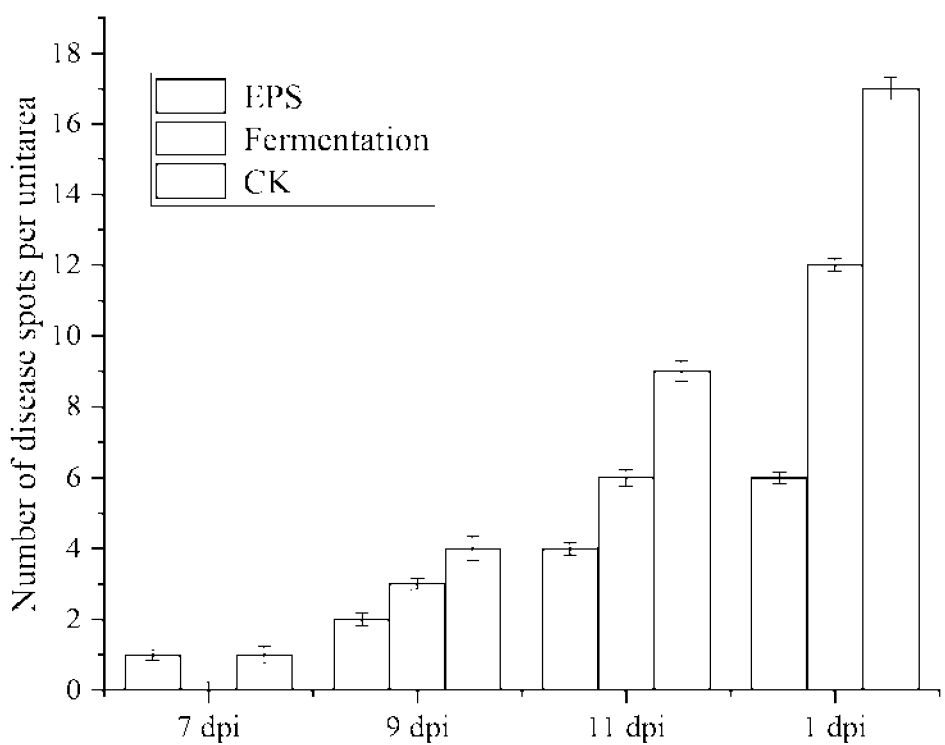
FIG. 14 is a detection diagram of inducing rice resistance to rice blast spot by the exopolysaccharide from *Rhodopseudomonas palustris* GJ-22 in a preferred embodiment of the present invention.

The exopolysaccharide from *Rhodopseudomonas palustris* GJ-22 prepared in Example 1 was formulated into a 1 g/L solution and sprayed on healthy rice leaves grown for 2 weeks. The rice blast spore suspension was sprayed on the second day. The rice leaves were cultivated in an incubator with alternating light and dark, and the number of diseased spots on the rice leaves was observed at days 7, 9, 11 and 13 after spraying the rice blast spore suspension, as shown in FIG. 14. The supernatant and water of the fermentation broth of *Rhodopseudomonas palustris* were used for blank testing.

FIG. 14 showed that the exopolysaccharide from *Rhodopseudomonas palustris* GJ-22 could significantly enhance the inhibitory effect of rice on the rice blast fungus.

From Examples 3 to 6, it could be concluded that the exopolysaccharide from *Rhodopseudomonas palustris* GJ-22 could be used to promote the growth of tobacco and rice, and could also be used to prevent and control tobacco mosaic virus and rice blast.

The above are only preferred embodiments of the present invention and are not used to limit the present invention. For those skilled in the art, the present invention can have various modifications and changes. Any modification, equivalent replacement, improvement, etc., made within the spirit and principle of the present invention shall be included in the protection scope of the present invention.

The invention claimed is:

1. A method for preparing an exopolysaccharide from *Rhodopseudomonas palustris*, the method comprising the steps of:
   1) keeping a seed solution from *Rhodopseudomonas palustris* GJ-22 in a fermentation medium for fermentation culture to obtain a fermentation broth;
   2) centrifuging the fermentation broth to take the supernatant, which is treated by alcohol precipitation after removal of suspended matters by membrane filtration, and then collecting the pellet from alcohol precipitation by centrifugation to obtain crude polysaccharide using lyophilization;
   3) removing proteins from the crude polysaccharide using a protease enzymolysis method and a Sevag method, followed by dialysis treatment with distilled water to remove small molecules and organic solvent to obtain a polysaccharide sample;
   4) purifying the polysaccharide sample through an anion exchange column and a molecular exclusion chromatography column in sequence to obtain the exopolysaccharide from *Rhodopseudomonas palustris*.

2. The method for preparing the exopolysaccharide from *Rhodopseudomonas palustris* according to claim 1, wherein in step 1), the components of the fermentation medium comprise: $(NH_4)_2SO_4$ 0.1 g, $MgSO_4$ 0.02 g, $Na_2CO_3$ 0.5 g, $K_2HPO_4$ 0.05 g, NaCl 0.02 g, casein amino acid 0.2 g, agar 1.5 g, at pH of 7.0-7.5,
the fermentation culture is carried out with a light intensity of 7000 lx-8000 lx at the temperature of 30° C. for 10 days.

3. The method for preparing the exopolysaccharide from *Rhodopseudomonas palustris* according to claim 2, wherein in step 2), the alcohol precipitation comprises the steps of adding anhydrous ethanol at a volume of twice that of the filtered supernatant with a placement at 4° C. for 24 h following stirring well,
collecting by centrifugation with a centrifugal force of 10000-13000 g at 4° C. for 20 min.

4. The method for preparing the exopolysaccharide from *Rhodopseudomonas palustris* according to claim 2, wherein in step 3), the protease enzymolysis method comprises the steps of: dissolving the crude polysaccharide obtained in step (2) in deionized water with addition of papain to obtain a sample, which is adjusted to pH 6.0-6.2 and treated in a water bath at 60° C. for 6 h, during which the obtained sample is shaken once every 1 hour for mixing well, with addition of anhydrous ethanol at a volume of twice that of the obtained sample after cooling, and then collecting the pellet by centrifugation after placement.

5. The method for preparing the exopolysaccharide from *Rhodopseudomonas palustris* according to claim 2, wherein the dialysis treatment uses a dialysis bag with a molecular weight cut-off of 8000 D-14000 D.

6. A method for promoting the growth of tobacco or rice, the method comprising
obtaining an exopolysaccharide by the method of claim 1 and
applying the exopolysaccharide to tobacco or rice leaves.

7. A method for preventing and controlling tobacco mosaic virus or rice blast, the method comprising
obtaining an exopolysaccharide by the method of claim 1 and
applying the exopolysaccharide to tobacco or rice leaves.

8. The method for preparing the exopolysaccharide from *Rhodopseudomonas palustris* according to claim 3, wherein collecting by centrifugation with a centrifugal force of 10000 g.

* * * * *